(12) United States Patent  
Govari et al.

(10) Patent No.: US 12,156,736 B2  
(45) Date of Patent: Dec. 3, 2024

(54) REAL TIME REMOVAL OF EP PARAMETER OUTLIERS FROM VISUAL MAP

(71) Applicant: BIOSENSE WEBSTER (ISRAEL) LTD., Yokneam (IL)

(72) Inventors: Assaf Govari, Haifa (IL); Yair Palti, Herzelia (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 525 days.

(21) Appl. No.: 17/036,227

(22) Filed: Sep. 29, 2020

(65) Prior Publication Data

US 2022/0095942 A1     Mar. 31, 2022

(51) Int. Cl.
A61B 5/287 (2021.01)
A61B 5/00 (2006.01)
A61B 5/339 (2021.01)
G06T 11/60 (2006.01)

(52) U.S. Cl.
CPC ............. *A61B 5/287* (2021.01); *A61B 5/339* (2021.01); *A61B 5/7221* (2013.01); *G06T 11/60* (2013.01); *G06T 2210/41* (2013.01)

(58) Field of Classification Search
CPC ............................... A61B 5/287; A61B 5/339
USPC ........................................................ 600/523
See application file for complete search history.

(56) References Cited

U.S. PATENT DOCUMENTS 8,812,091 B1   8/2014 Brodnick
9,949,657 B2   4/2018 Ravuna
10,398,348 B2   9/2019 Osadchy
2003/0004411 A1 * 1/2003 Govari .................. A61B 5/061
                                                              600/424
2012/0101398 A1   4/2012 Ramanathan
2015/0057507 A1   2/2015 Koyrakh
2017/0311833 A1  11/2017 Afonso
(Continued)

FOREIGN PATENT DOCUMENTS

CA          3006816 A1 * 12/2018 ............. A61B 5/063
WO   WO2020185339 A1    9/2020

OTHER PUBLICATIONS

European Search Report for corresponding EPA No. 21199564.2 dated Feb. 25, 2022.

*Primary Examiner* — Nicole F Lavert

(57) ABSTRACT

A medical apparatus includes a probe configured for insertion into a body of a patient. The probe includes electrodes configured to contact tissue of a region within the body. The apparatus further includes a display screen a position-tracking system, and a processor. The processor is configured to acquire electrophysiological signals from the electrodes, to extract electrophysiological parameters from the signals, to compute a measure of consistency of the electrophysiological parameters at each of the locations with respect to a weighted median of the parameters extracted at neighboring locations, and to render to the display screen a map of the tissue while overlaying on the map a visual indication of the extracted electrophysiological parameters for which the measure of consistency satisfied a predefined consistency criterion, and automatically omitting from the map the electrophysiological parameters for which the measure of consistency did not satisfy the criterion.

8 Claims, 5 Drawing Sheets

(56) References Cited

U.S. PATENT DOCUMENTS

2018/0014751 A1* 1/2018 Hill .................. A61B 5/283
2019/0328258 A1 10/2019 Gaeta

* cited by examiner

REAL TIME REMOVAL OF EP PARAMETER OUTLIERS FROM VISUAL MAP

FIELD OF THE INVENTION

The present invention relates generally to electrophysiological measurements, and particularly to apparatus and methods for automated mapping of electrophysiological parameters.

BACKGROUND

An electrophysiological (EP) map of tissue of a patient is generated by positioning one or more electrodes on a region of the tissue, acquiring an EP signal of the region, and then repeating the process for a different region. EP parameters are extracted from the EP signals in each region of measurement, and then displayed over an image or other graphical representation of the tissue.

For example, U.S. Pat. No. 9,949,657, whose disclosure is incorporated herein by reference, describes a method for displaying electroanatomical information. The method comprises identifying at least one multiple-activation area of a surface of a heart, at which multiple-activation area were recorded at least two different local activations during a single cardiac cycle of the heart. The multiple-activation area is displayed, on an electroanatomical map of the surface of the heart, in a manner that indicates a time difference between respective times of the two local activations.

SUMMARY

Embodiments of the present invention that are described hereinbelow provide improved methods and apparatus for mapping of EP parameters.

There is provided, in accordance with an exemplary embodiment of the present invention, a medical apparatus, which includes a probe configured for insertion into a body of a patient, wherein the probe includes one or more electrodes configured to contact tissue of a region within the body. The apparatus further includes a display screen, a position-tracking system configured to acquire position coordinates of the one or more electrodes within the body, and a processor. The processor is configured to acquire respective electrophysiological signals from the one or more electrodes while the one or more electrodes contact multiple locations in the region, to extract respective electrophysiological parameters from the electrophysiological signals, and to compute a respective measure of consistency of the respective electrophysiological parameters at each of the locations with respect to a weighted median of the electrophysiological parameters extracted at neighboring locations.

The processor is further configured to render to the display screen, responsively to the position coordinates, a map of the tissue while overlaying on the map a visual indication of the extracted electrophysiological parameters for which the respective measure of consistency satisfied a predefined consistency criterion, and automatically omitting from the map the electrophysiological parameters for which the respective measure of consistency did not satisfy the predefined consistency criterion.

In a disclosed embodiment, for any given location, the neighboring locations are selected such that respective distances from the given location to the neighboring locations are within a predefined radius.

In another embodiment, the processor is configured to compute the respective measure of consistency for any given location by computing a difference between an electrophysiological parameter extracted at the given location and the weighted median of the electrophysiological parameters extracted at neighboring locations.

In a further embodiment, the predefined consistency criterion is satisfied when the computed difference does not exceed a predefined threshold.

In a disclosed embodiment, the processor is configured to compute the weighted median by applying weights to the electrophysiological parameters extracted at the neighboring locations using a weighting function selected from a list of weighting functions consisting of a distance weighting function, a confidence weighting function, and a variance weighting function.

In a further embodiment, for any given location, the distance weighting function applies a weight that decreases with increasing distance between the given location and the neighboring locations. Additionally or alternatively, the confidence weighting function is computed for each given neighboring location responsively to a number of times an electrophysiological signal has been acquired at the given neighboring location. Also additionally or alternatively, the variance weighting function applies a weight that decreases with increasing variance of the electrophysiological parameters projected to the neighboring location.

In a disclosed embodiment, the processor is configured to compute and render to the display screen a spatially continuous distribution of the electrophysical parameters in the region by interpolating only the electrophysiological parameters extracted at the locations for which the respective measure of consistency satisfied the predefined consistency criterion.

In yet another embodiment, the electrophysiological parameters include a local activation time (LAT) in a heart of the patient. Additionally or alternatively, the electrophysiological parameters include an electrophysiological voltage in a tissue of the patient.

There is also provided, in accordance with an embodiment of the present invention, a method for electrophysiological mapping. The method includes acquiring respective electrophysiological signals from one or more electrodes while the one or more electrodes contact tissue at multiple locations in a region within a body of a patient, acquiring position coordinates of the one or more electrodes at each of the locations within the body, extracting respective electrophysiological parameters from the electrophysiological signals at each of the locations, and computing a respective measure of consistency of the respective electrophysiological parameters at each of the locations with respect to a weighted median of the electrophysiological parameters extracted at neighboring locations. The method further includes rendering to the display screen, responsively to the position coordinates, a map of the tissue while overlaying on the map a visual indication of the extracted electrophysiological parameters for which the respective measure of consistency satisfied a predefined consistency criterion, and automatically omitting from the map the electrophysiological parameters for which the respective measure of consistency did not satisfy the predefined consistency criterion.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
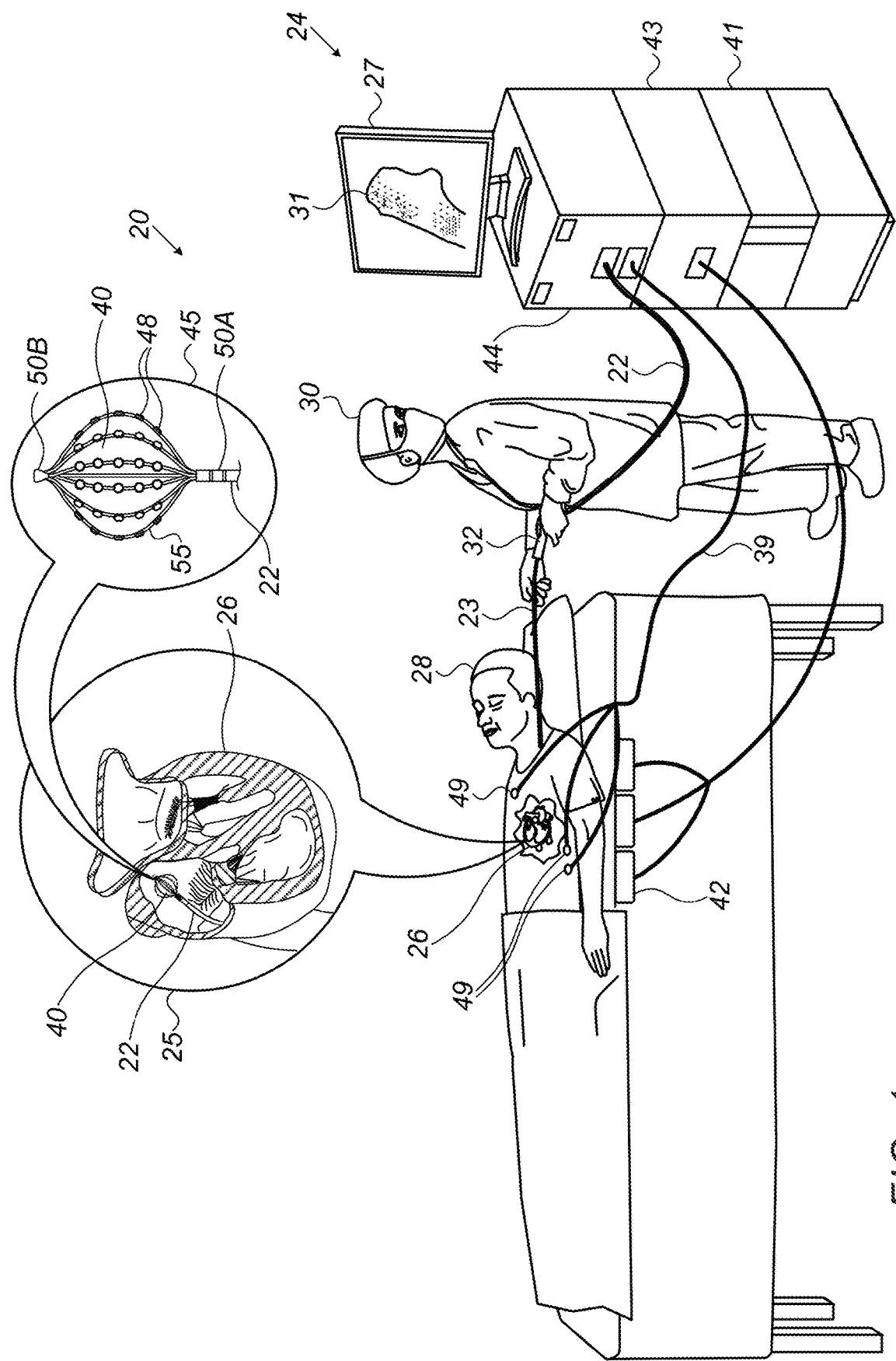
FIG. 1 is a schematic pictorial illustration of a medical apparatus for mapping an EP parameter in a heart of a patient, in accordance with an exemplary embodiment of the present invention.

To generate an electrophysiological (EP) map of a tissue of a patient (electroanatomical mapping), a physician positions a probe so that one or more electrodes on the probe contact a region of the tissue. The probe acquires EP signals from the region, and the process is then repeated over other regions. From each location in the region where a signal is acquired, a processor analyzes the signal to extract an EP parameter for the location, for example a local activation time (LAT) in a chamber of the heart or an EP voltage in the tissue. The EP parameter values are then overlaid on a visual three-dimensional (3D) map of the region, for example as a color code, to form an EP parameter map, which can be viewed by the physician. The mapping may be performed in real time.

At some locations in the region, the extracted values of the EP parameters may not be consistent with the EP parameters at neighboring locations. These values are called "outliers" or "outlying values." Such outliers may be due to, for example, a noisy EP signal at a certain location in the region. The outliers may skew the EP parameter map, thus giving the physician incorrect information regarding the distribution of the EP parameters across the region. Even if the acquisition of the EP signals is repeated, the outlying value may still skew the visual map if there is no facility for deleting these problematic EP parameter values.

The embodiments of the present invention that are described herein address these problems by providing a medical apparatus, methods and software that automatically detect and omit outliers from an EP map. Specifically, EP parameters at a given location that do not satisfy a consistency criterion when compared with a median of the EP parameters at neighboring locations are omitted from the map.

In the disclosed embodiments, the apparatus comprises a probe, a display screen, a position-tracking system, and a processor. The probe, comprising one or more electrodes, is inserted into the body of a patient so that the electrodes contact tissue of a region within the body, for example in a chamber of the heart. The position-tracking system acquires position coordinates of the electrodes within the body. The processor acquires EP signals from the electrodes while the electrodes contact multiple locations in the region, and extracts EP parameters from the signals. The processor computes a measure of consistency of the EP parameters extracted at each of the locations with respect to a weighted median of the EP parameters extracted at neighboring locations. The processor renders to the display screen a 3D map of the tissue with an overlaid visual indication of the extracted EP parameters according to their position coordinates for those locations where the measure of consistency satisfies a predefined consistency criterion, while automatically omitting the EP parameters for which the respective measure of consistency did not satisfy the consistency criterion.

For the purpose of computing the measure of consistency at a selected location, the neighboring locations can be defined, for example, as locations within a predefined radius of the selected location. In some embodiments, the processor computes the measure of consistency as the difference between the EP parameter extracted at the selected location and a weighted median of the EP parameters extracted at the neighboring locations. Alternatively, other measures of consistency may be used, for example a normalized difference relative to the weighted median. When the measure of consistency does not exceed a predefined threshold, the EP parameter extracted at the selected location is considered to satisfy the consistency criterion, i.e., not to be an outlier.

Typically, the processor computes the weighted median using one or a combination of the following weighting functions: a distance weighting function, a confidence weighting function, and a variance weighting function; but alternatively, other weighting functions may be used. Alternatively, the weights may be preset to certain suitable values, including applying equal weights to all the neighboring locations participating in the weighted median.

For purposes of rendering the EP map, the processor typically computes a spatially continuous distribution of the EP parameter in the region by interpolating over the extracted EP parameters at the locations for which the measure of consistency satisfied the predefined consistency criterion (i.e., where the EP parameters are not outliers). This spatially continuous distribution is overlaid on the 3D map and effectively replaces the outliers in the map with interpolated values, thus avoiding the errors in the map that would otherwise arise.

System Description

FIG. 1 is a schematic pictorial illustration of a medical apparatus 20 for mapping an EP parameter in a heart 26 of a patient 28, in accordance with an embodiment of the present invention. The embodiment shown in the current figure and subsequent figures refers to an example of acquiring EP signals from a chamber of heart 26. In alternative embodiments, the values of EP parameters may be acquired using other sorts of mapping apparatus, not only from the heart, but also from other organs and tissue, as will be apparent to those skilled in the art after reading the present description.

A physician 30 navigates a catheter 40 to a target location in heart 26 (inset 25) of patient 28, by manipulating a shaft 22, using a manipulator 32 near the proximal end of the catheter, and/or deflection from a sheath 23. In the pictured example, catheter 40 comprises a basket assembly at its distal end, as shown in an inset 45, but alternatively other types of catheters may be used, as are known in the art. In the embodiment seen in an inset 25, physician 30 uses catheter 40 to perform electroanatomical mapping of a chamber of heart 26. EP signals are acquired from tissue by bringing electrodes 48 on catheter 40 into contact with the tissue within the heart, as further detailed below.

Catheter 40 is inserted in a collapsed configuration, through sheath 23, and only after the catheter exits sheath 23 does the catheter expand to its intended functional shape, as shown in inset 45. By containing catheter 40 in a collapsed configuration, sheath 23 also serves to minimize vascular trauma on its way to the target location.

For purposes of position tracking, catheter 40 incorporates a magnetic sensor 50A, seen in inset 45, at the distal end of shaft 22 (i.e., at the proximal end of the basket assembly). Typically, although not necessarily, sensor 50A is a Triple-Axis Sensor (TAS), comprising three miniature coils oriented in different directions. In the pictured embodiment, a second magnetic sensor 50B is incorporated in at the distal end of the basket assembly. Sensor 50B may be a Single-Axis Sensor (SAS) or a Triple-Axis Sensor (TAS), for example. Alternatively, catheter 40 may comprise other sorts of magnetic sensors, at these or other locations. Alternatively or additionally, the catheter may comprise other sorts of position sensors, such as impedance-based or ultrasonic position sensors, as are known in the art.

The basket assembly at the distal end of catheter 40 comprises multiple expandable spines 55, which are mechanically flexible. Multiple electrodes 48 are fixed to each spine, for a total of, for example, 120 electrodes. Electrodes 48 are configured to touch the tissue of patient 28 for sensing EP signals. Magnetic sensors 50A and 50B and electrodes 48 are connected by wires (not shown) running through shaft 22 to various processing circuits in a console 24.

Alternatively, apparatus 20 may comprise other types of catheters, with other sorts of electrode arrays, such as an inflatable balloon catheter with electrodes 48 on its outer surface, or a catheter having one or more flexible arms at its distal end.

Medical apparatus 20 comprises a magnetic position-tracking sub-system 43 in console 24 for determining the position and orientation of the distal end of catheter 40, and thereby the positions of electrodes 48. Patient 28 is placed in a magnetic field generated by a pad containing magnetic field generator coils 42, which are driven by position-tracking sub-system 43. The magnetic fields generated by coils 42 give rise to electrical signals in sensors 50A and 50B, which are indicative of the position and orientation of the sensors. The signals from sensors 50A and 50B are transmitted back to position-tracking sub-system 43, which converts the signals to corresponding digital inputs to a processor 41. Processor 41 uses these inputs to compute the position and orientation of the distal end of catheter 40 and thus to find the respective location of each of electrodes 48.

Methods of position and/or orientation sensing using external magnetic fields and magnetic sensors, such as sensors 50A and 50B, are implemented in various medical applications, for example, in the CARTO® system, available from Biosense Webster, Inc. (Irvine, California). Such methods are described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

Alternatively or additionally, as noted above, apparatus 20 may use other methods of position sensing to find the locations of electrodes 48. For example, processor 41 may map the locations of electrodes 48 by measuring impedances between electrodes 48 and body-surface electrodes 49, which are placed on the chest of patient 28 and connected to console 24 by leads 39.

Processor 41 additionally receives EP signals from electrodes 48 on catheter 40 via an electrical interface 44, and uses the information contained in these signals together with the coordinates provided by magnetic sensors 50A and 50B to construct an electroanatomical map 31 of the chamber of heart 26 in which catheter 40 is located. During and/or following the procedure, processor 41 may render electroanatomical map 31 to a display screen 27.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the disclosed steps, as described below.

The example illustration shown in FIG. 1 is chosen purely for the sake of conceptual clarity. FIG. 1 shows only elements related to the disclosed techniques for the sake of simplicity and clarity. Medical apparatus 20 typically comprises additional modules and elements that are not directly related to the disclosed techniques, and thus are intentionally omitted from FIG. 1 and from the corresponding description. The elements of medical apparatus 20 and the methods described herein may be further applied, for example, to control an ablation of tissue of heart 26.

Determination of Outliers and Displaying EP Parameters

Figure 2:
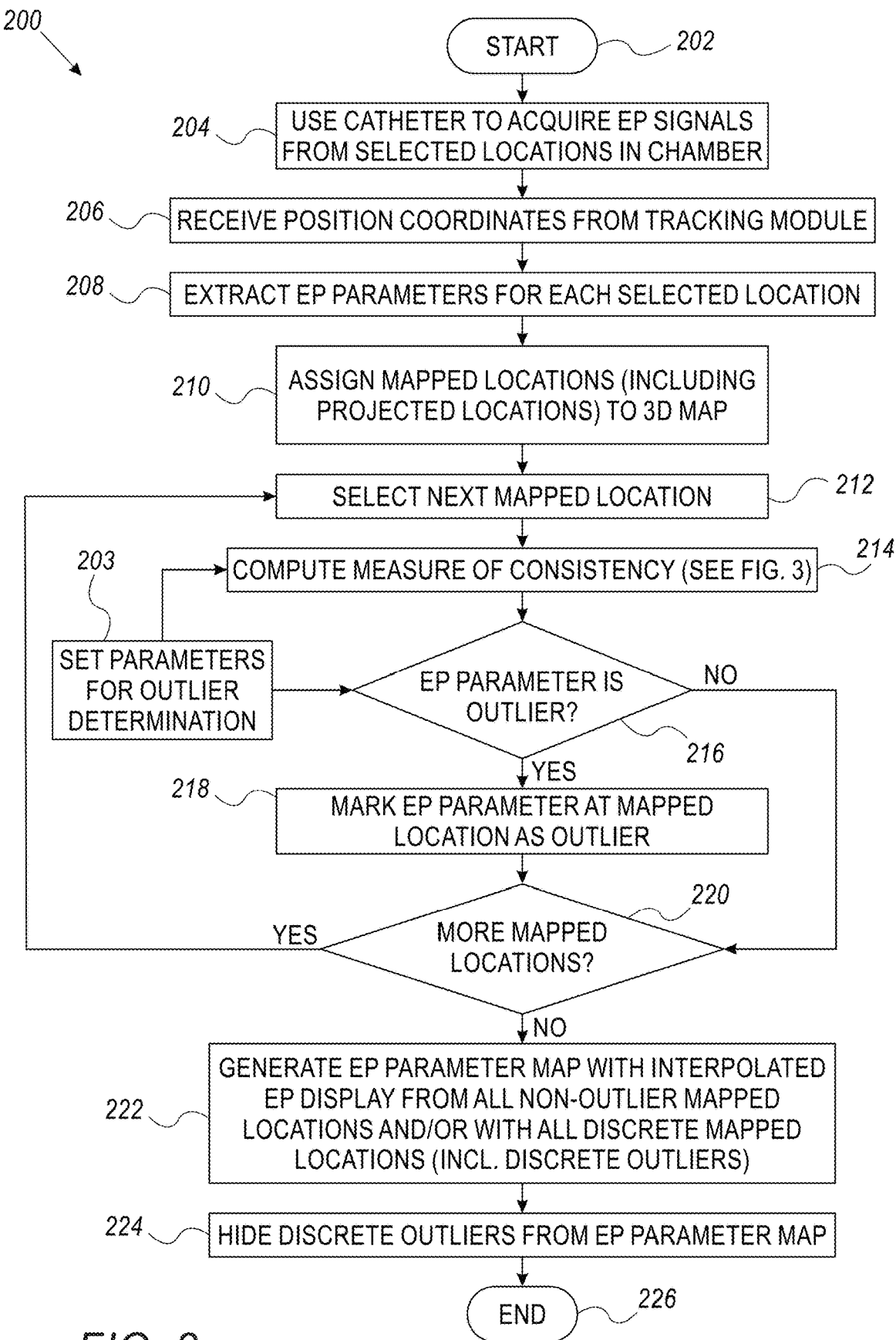
FIGS. 2 and 3 are flowcharts that schematically illustrate an automated process for identifying and removing outliers from an EP map, in accordance with an exemplary embodiment of the invention.
Figure 3:
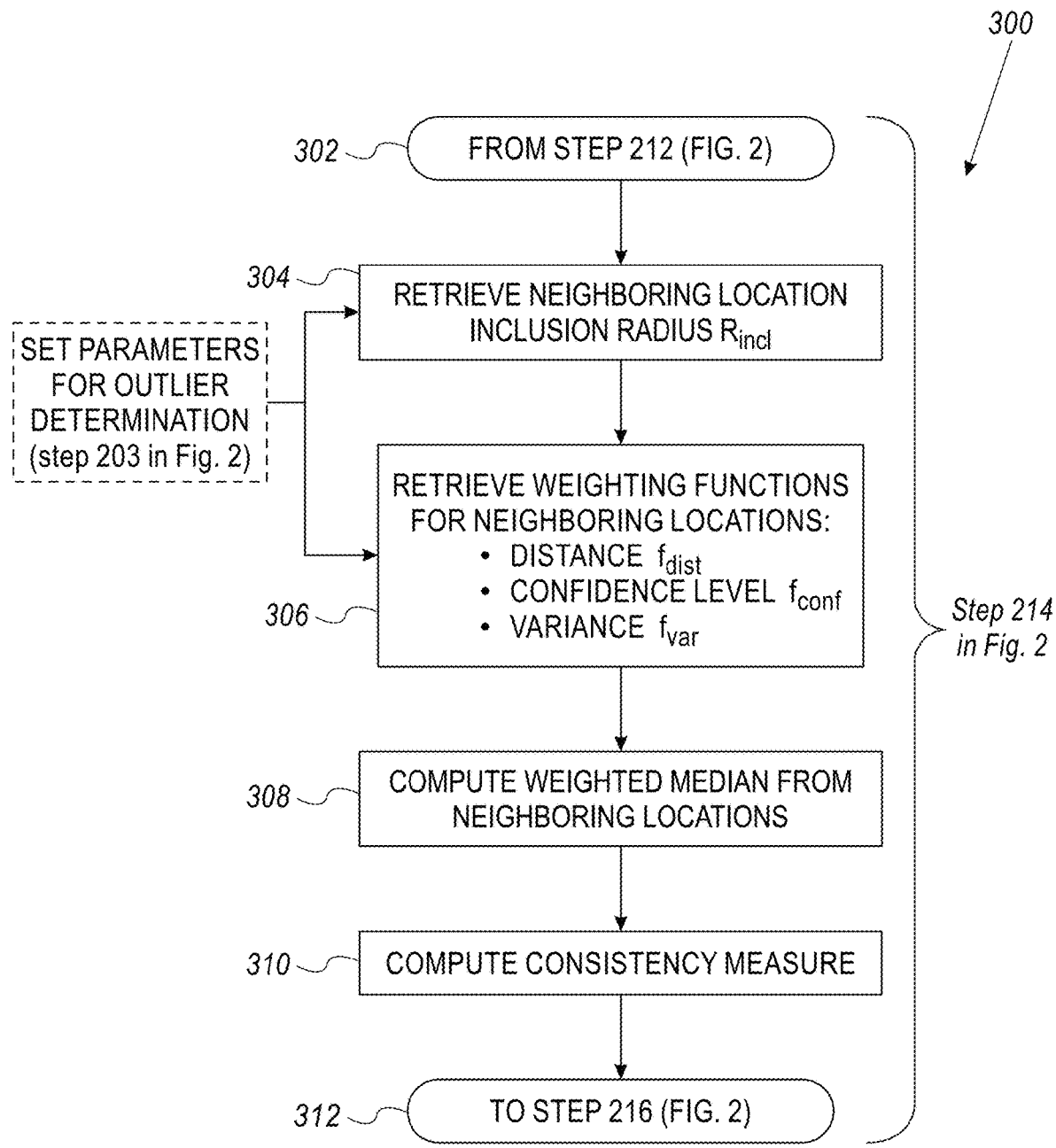

FIGS. 2 and 3 are flowcharts 200 and 300, respectively, that schematically illustrate an automated process for identifying and removing outliers from an EP map, in accordance with an exemplary embodiment of the invention. Flowchart 200 illustrates the overall process for acquiring and extracting EP parameters and identifying and removing the outliers from an EP parameter map, whereas flowchart 300 illustrates the computation of a measure of consistency that is used in identifying outliers. The process is described here, for the sake of concreteness and clarity, with reference to the elements of apparatus 20 (FIG. 1). Alternatively, the principles of this method may be applied, mutatis mutandis, in other system configurations, including configurations in which the EP signals are processed by a remote server, which communicates with the mapping apparatus via a network.

Referring to FIG. 2, the process for acquiring and extracting EP parameters and identifying and removing the outliers from an EP parameter map starts at a start step 202. In a parameter setting step 203, the parameters used in a consistency measure step 214 and in a decision step 216 are set. These parameters will be detailed below and in FIG. 3.

In an acquisition step 204, EP signals are acquired, with reference to FIG. 1, by processor 41 from heart 26 through electrodes 48 of catheter 40.

In a tracking step 206, processor 41 receives signals from tracking module 43, and computes the respective location coordinates of electrodes 48.

In an extraction step 208, processor 41 extracts the respective EP parameters from the acquired signals. For example, processor 41 may compute a local activation time (LAT) for each location by finding the time (relative to a reference time) at which the peak or the sharpest slope occurs in the signal measured at the location. Alternatively or additionally, processor 41 may compute the peak amplitude of the signal at each location and/or any other signal parameter of interest.

In a location assignment step 210, processor 41 assigns the EP parameters extracted at given locations in the heart (discrete EP parameters) to corresponding locations on a 3D map of the chamber of heart 26, based on the position coordinates received in tracking step 206. The 3D map is generated, for example, from an image of the heart previously stored in the processor and/or on the position measurements taken in tracking step 206.

On occasion, one (or more) of electrodes 48 may not be touching the surface of heart 26 while acquiring EP signals. In such a case, the position coordinates of the specific electrode 48, as received in tracking step 206, do not coincide with the surface of heart 26, and the mapped location is "detached" from the surface. The term "mapped location" is used in the following description, for brevity, to denote a location in the heart at which an EP parameter has been extracted. In order to assign such a mapped location to the 3D map of heart 26, the location in the heart is projected onto the closest location on the surface of the heart, and this location in the heart is now assigned to the mapped location and displayed on the EP parameter map. As catheter 40 with multiple electrodes 48 travels over the surface of the tissue of heart 26, possibly several times, multiple "detached" mapped locations may be projected onto the same location om the surface. In such a case, a median value of the EP parameters projected to the same location is used for that location.

In a selection step 212, processor 41 selects a mapped location for determining whether the EP parameter extracted at that location is an outlier, i.e., whether its measure of consistency does or does not satisfy the consistency criterion. The mapped location is selected from those locations, including projected locations, that have not yet been processed in consistency measurement step 214. In step 214, processor 41 computes the measure of consistency for the EP parameter extracted at the mapped location selected in selection step 212. For example, the measure of consistency may be proportional to the difference between the EP parameter at the given location and a weighted median of the respective EP parameters at a set of neighboring locations, as detailed in FIG. 3. In this case, a large measure of consistency indicates that the EP parameter at the given location is not consistent with its neighbors, and vice versa. Alternatively, the measure of consistency may be defined such that the value is large when the EP parameter at a given location is consistent with its neighbors, and small when the EP parameters are inconsistent.

In decision step 216, processor 41 evaluates the measure of consistency from step 214 against a predefined consistency criterion. For example, the measure of consistency may be compared to a threshold that was defined in parameter setting step 203. Assuming the measure of consistency was defined to increase with the difference between a given location and its neighbors, if the measure of consistency exceeds the threshold, the EP parameter extracted at the selected location does not satisfy the consistency criterion. In this case, the EP parameter is deemed to be an outlier, and the automated process is directed to an outlier marking step 218. Although in decision step 216, the difference between the measure of consistency and the threshold is used as the consistency criterion, other criteria may alternatively be used, as noted earlier.

In outlier marking step 218, processor 41 marks the EP parameter extracted at the selected mapped location as an outlier, and the process continues to an additional location step 220. The marking may comprise, for instance, processor 41 adding an indicator flag to a list of mapped locations in its memory.

If the EP parameter extracted at the selected mapped location was deemed not to be an outlier in decision step 216, the automated process continues directly to additional location step 220.

In additional location step 220, processor 41 determines whether there still are locations among the mapped locations that have not been processed through consistency measure step 214. If so, the process returns to selection step 212. If there are no more such locations, the process continues to a continuous display revision step 222.

In a map generation step 222, processor 41 generates an EP parameter map of the chamber of heart 26. The 3D map of the chamber (from step 210) is overlaid with either or both of the EP parameters extracted at given locations and an interpolated map of the EP parameters, as further described below. At this stage of the process, all mapped locations, including those having possibly outlying EP parameters, are displayed. However, only non-outlier mapped locations are utilized for the interpolated map.

Processor 41 displays the EP parameters extracted at given locations (discrete EP parameters) on the EP parameter map, based on step 210, for example as small, color-coded circles (or some other suitable shapes). The color-coding may comprise, for example, showing the lowest value of the EP parameter as a blue color, the highest value as a red color, and intermediate values between the lowest and highest values in the same order as colors in the visible spectrum. However, other color-coding schemes, as well as shading or symbols, as are known in the art, may alternatively be used.

Additionally or alternatively, processor 41 computes and displays a spatially continuous map of the EP parameters by interpolating over the non-outlier EP parameters extracted at given locations. The continuous map typically uses the same color-coding as used in displaying the discrete EP parameters.

The display of the EP parameter map on display screen 27 may be controlled by physician 30.

In an outlier removal step 224, the outliers marked in outlier marking step 218 (also denoted as "discrete outliers") are removed from the EP parameter map, so that the map displays only non-outlier EP parameters at their respective locations. As a result of steps 222 and 224, the revised EP parameter map of the surface of the chamber includes only non-outlier extracted EP parameters and an interpolated map computed only from these EP parameters. In other words, processor 41 computes a spatially continuous distribution of the electrophysical parameters in the heart chamber by interpolating only the electrophysiological parameters extracted at the locations for which the respective measure of consistency satisfied the consistency criterion. The display of the revised EP parameter map (without discrete outliers) on display screen 27 may again be controlled by physician 30.

The automated process comes to an end in an end step 226.

Referring now to FIG. 3, flowchart 300 shows details of the computation of the measure of consistency for an EP parameter extracted at a selected mapped location. In flowchart 200 in FIG. 2, this process is represented as consistency measure step 214. In computing the consistency measure for an EP parameter extracted at a selected mapped location, the impact of the EP parameters extracted at neighboring locations is taken into account both by defining the neighboring locations, as detailed below in a radius retrieval step 304, and by weighting their impact, as detailed below in a weighting function retrieval step 306 and in an expected EP parameter step 308.

The process starts in a start step 302, where the selected mapped location from step 212 in FIG. 2 is received. In radius retrieval step 304, an inclusion radius $R_{incl}$ for defining neighboring locations is retrieved from parameter step 203 in FIG. 2. For example, a sphere is defined with the selected mapped location as its center and $R_{incl}$ as its radius. All locations inside this sphere are defined as "neighboring locations," and will be included in determining whether the selected location is an outlier.

In a weighting function retrieval step 306, processor 41 retrieves the weighting function (detailed further below) from step 203. In a weighted median computation step 308, processor 41 computes a weighted median of the EP parameters extracted at the neighboring locations (locations within radius $R_{incl}$), by applying the appropriate weight, as indicated by the weighting function, to each of the EP parameter values. The term "weighted median" is used in the present description and in the claims in its conventional sense in the statistical arts. Specifically, given a set of values of an EP parameter $x_i$ at respective neighboring locations $L_i$, $\{x_1(L_1), x_2(L_2), \ldots, x_n(L_n)\}$, with the values arranged in increasing order, and with respective weights $\{w_1, w_2, w_n\}$, such that $\Sigma_{i=1}^2 w_i = 1$, the weighted median will be the value $x_k$ that satisfies:

$$\sum_{i=1}^{k-1} w_i \leq 1/2$$

and $$\sum_{i=k+1}^{n} w_i \geq 1/2$$

When all the weights are equal, the weighted median is equal to the simple median of $\{x_1(L_1), x_2(L_2), \ldots, x_n(L_n)\}$.

Processor 41 uses the weighted median in a consistency measurement step 310 to compute the measure of consistency as the difference between the EP parameter extracted at the selected mapped location and the weighted median of the EP parameters extracted at the neighboring locations. The process in flowchart 300 ends in an end step 312, passing the consistency measure to step 216 in FIG. 2.

Weighting Functions

Any suitable weighting function or combination of functions may be chosen at retrieval step 306. The examples shown in FIG. 3 include a distance weighting function $f_{dist}$, a confidence weighting function $f_{conf}$, and a variance weighting function $f_{var}$, which are retrieved from parameter step 203.

Using the distance weighting function $f_{dist}$, processor 41 computes the weights so as to take into account the influence of the distance of a neighboring location from the selected location on the weighted median. In one embodiment, the weight of an EP parameter extracted at a given neighboring location i is defined as $f_{dist} = (1 - r_i/R_{incl})/A_{dist}$ wherein $r_i$ is the distance between location i and the selected location, and $A_{dist}$ normalizes the sum of the weights defined by $f_{dist}$ to one. Thus, an EP parameter extracted at a neighboring location closer to the selected location has a higher weight than an EP parameter extracted at a neighboring location further from the selected location.

Using the confidence weighting function $f_{conf}$, processor 41 computes the weights based on a confidence level of the EP parameter extracted at a neighboring location. The confidence level at a neighboring location is influenced, inter alia, by the number of times an EP signal is acquired at a given location due to repeated measurements by an electrode 48. In one embodiment, the confidence weighting function $f_{conf}$ for an EP parameter extracted at a neighboring location i is defined as $f_{conf} = n_i/N$, wherein $n_i$ refers to the number of times a signal has been sampled at the location i, and N refers to the total number of signals sampled. Thus, for example, an EP parameter extracted in a neighboring location from a signal sampled four times has four times the confidence level of an EP parameter extracted in another neighboring location from a signal sampled only once. Alternatively or additionally, other measures of confidence may be used, such as the location stability, pressure, or impedance measured during signal acquisition at each of the neighboring locations.

Using the variance weighting function $f_{var}$, processor 41 computes the weights due to a variance between multiple EP parameters extracted at neighboring locations, when these locations are projected to the same location on the surface of heart 26, as described in step 210 in FIG. 2. The smaller the variance between these EP parameters, the higher the impact of these EP parameters on the computation of the measure of consistency. In one embodiment, the variance weighting function $f_{var}$ at a location i on the surface of heart 26 is defined as $f_{var} = 1 - (\sigma_i^2/A_{var})$, where $\sigma_i^2$ refers to the variance of the EP parameters extracted at locations that are projected onto location i, and $A_{var}$ is a factor normalizing the sum of the weights to one. The variance weighting function $f_{var}$ may be further modified to take into consideration the number of mapped locations projected to the same location. For example, were two locations to exhibit the same variance but a contribution from a dissimilar number of projected locations, the location with a higher number of projected locations would have a higher weight in the computation of weighted median.

In alternative embodiments, other forms of the weighting functions, either continuous or discrete, may be used.

In setting the weighting functions in parameter step 203 in FIG. 2, the relative impacts of the three weighting functions of distance, confidence, and variance may be selected. For example, only one of the weighting functions, or alternatively any combination of the weighting functions, may be included in the computation of an outlier by suitably combining the three weighting functions $f_{dist}$, $f_{conf}$, and $f_{var}$ to a composite weighting function $f_{composite}$. In any case, the weighting functions are normalized so that the composite weights over each set of neighboring locations sum to 1.

Rendering the Map

Figure 4A:
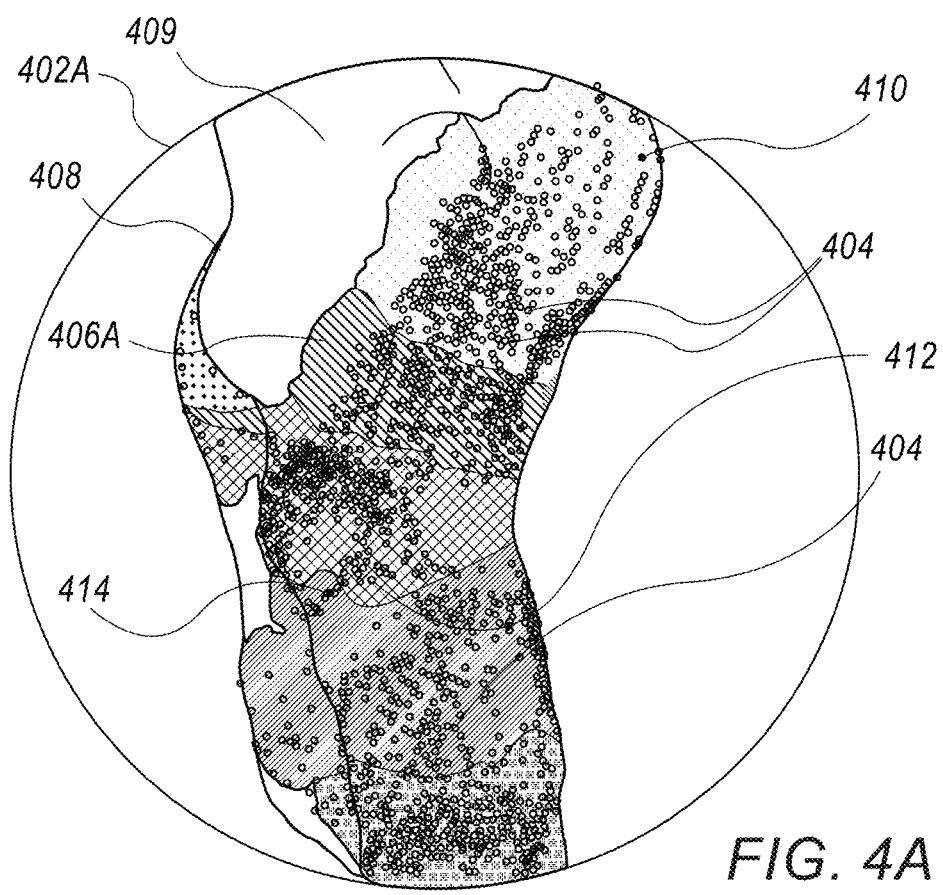
FIGS. 4A and 4B are schematic representations of EP maps illustrating two phases of a process of outlier removal, in accordance with an exemplary embodiment of the invention.
Figure 4B:
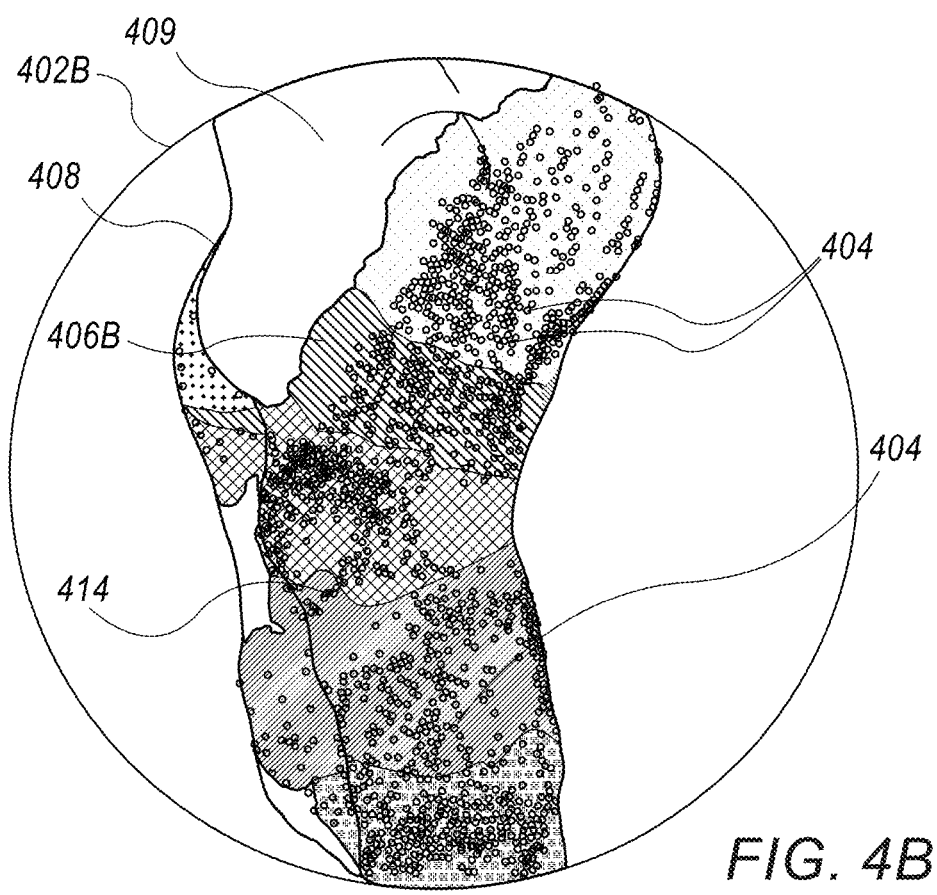

FIGS. 4A and 4B are schematic representations of EP parameter maps 402A and 402B, respectively, illustrating two phases in the process of outlier removal, in accordance with an embodiment of the invention. Maps 402A and 402B are both based on a 3D map 408 of the same region of a chamber of heart 26, and with the same continuous map of the values of the EP parameter, as interpolated from the non-outlier EP parameters. The difference between the two maps is that map 402A displays all discrete mapped locations, including outliers, whereas map 402B displays only the non-outlier discrete mapped locations.

FIG. 4A shows EP parameter map 402A with multiple mapped locations 404 of the EP parameter, for example LAT, overlaid on 3D map 408. Mapped locations 404 are displayed as small circles, with the value of the respective EP parameter shown by color-coding, as described in map generation step 222 in FIG. 2. FIG. 4A also shows an area 406A on map 402A that displays a continuous map of the values of the EP parameter, as interpolated from the non-outlier EP parameters extracted at mapped locations 404. Area 406A is color-coded with the same coding as the EP parameters extracted at mapped locations 404. An area 409 on map 402A is displayed as a uniform neutral color, such as grey, signifying that neither mapped locations 404 nor area 406A (the interpolated map) extend to this part of 3D map 408, and consequently this area does not display any values of the EP parameter.

The EP parameters extracted at mapped locations 410 and 412 have been marked by the automated process to be outliers (step 218 in FIG. 2), but they have been left in FIG. 4A in case physician 30 wishes to explore them further. These mapped locations may also at this stage be visually judged to be outliers due to their differences from the EP parameters extracted at the respective neighboring mapped locations. Although the EP parameter extracted at mapped location 414 looks superficially similar to that at mapped location 412, however, it is not an outlier, as several of its immediate neighbors have the same value of the EP parameter. Map 402A corresponds to the stage immediately after map generation step 222 in flowchart 200 in FIG. 2, and its display on display screen 27 may be controlled by physician 30.

FIG. 4B shows the same areas and locations as FIG. 4A, except that the outliers (at mapped locations 410 and 412) have been removed. Area 406B, displaying the continuous interpolated EP parameters, is identical to area 406A in FIG. 4A. Map 402B corresponds in flowchart 200 to the stage after outlier removal step 224. As above, its display on display screen 27 may be controlled by physician 30.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
a position-tracking system configured to acquire position coordinates of the one or more electrodes of a probe in contact with tissue of a region within the body; and
a processor configured to:
acquire respective electrophysiological signals from the one or more electrodes while the one or more electrodes contact multiple locations in the region;
extract respective electrophysiological parameters from the electrophysiological signals, wherein the electrophysiological parameters comprise at least one of a local activation time (LAT) and an electrophysiological voltage in a heart of the patient;
compute a respective measure of consistency of the respective electrophysiological parameters at each of the locations with respect to a weighted median of the electrophysiological parameters extracted at neighboring locations, wherein the respective measure of consistency is a difference between the respective electrophysiological parameter at each of the locations location and the weighted median of the electrophysiological parameters extracted at the neighboring locations; and
generate, responsively to the position coordinates, a map of the tissue while overlaying on the map a visual indication of the extracted electrophysiological parameters for which the respective measure of consistency satisfied a predefined consistency criterion, and automatically omitting from the map the electrophysiological parameters for which the respective measure of consistency did not satisfy the predefined consistency criterion,
wherein for any given location, the neighboring locations are selected such that respective distances from the given location to the neighboring locations are within a predefined radius.

2. The medical apparatus according to claim 1, wherein the processor is configured to compute the respective measure of consistency for any given location by computing a difference between an electrophysiological parameter extracted at the given location and the weighted median of the electrophysiological parameters extracted at neighboring locations.

3. The medical apparatus according to claim 2, wherein the predefined consistency criterion is satisfied when the computed difference does not exceed a predefined threshold.

4. The medical apparatus according to claim 1, wherein the processor is configured to compute the weighted median by applying weights to the electrophysiological parameters extracted at the neighboring locations using a weighting function selected from a list of weighting functions consisting of a distance weighting function, a confidence weighting function, and a variance weighting function.

5. The medical apparatus according to claim 4, wherein for any given location, the distance weighting function applies a weight that decreases with increasing distance between the given location and the neighboring locations.

6. The medical apparatus according to claim 4, wherein the confidence weighting function is computed for each given neighboring location responsively to a number of times an electrophysiological signal has been acquired at the given neighboring location.

7. The medical apparatus according to claim 4, wherein the variance weighting function applies a weight that decreases with increasing variance of the electrophysiological parameters projected to the neighboring location.

8. The medical apparatus according to claim 1, wherein the processor is configured to compute and render to the display screen a spatially continuous distribution of the electrophysical parameters in the region by interpolating only the electrophysiological parameters extracted at the locations for which the respective measure of consistency satisfied the predefined consistency criterion.

* * * * *